(12) United States Patent
Schmaus et al.

(10) Patent No.: US 11,583,486 B2
(45) Date of Patent: Feb. 21, 2023

(54) COSMETIC EMULSION COMPRISING 1,2-DECANEDIOL

(71) Applicant: SYMRISE AG, Holzminden (DE)

(72) Inventors: Gerhard Schmaus, Höxter-Bosseborn (DE); Jan Peter Ebbecke, Halle (DE); Sabine Lange, Holzminden (DE)

(73) Assignee: SYMRISE AG, Holzminden (DE)

( * ) Notice: Subject to any disclaimer, the term of this patent is extended or adjusted under 35 U.S.C. 154(b) by 299 days.

(21) Appl. No.: 16/955,891

(22) PCT Filed: Dec. 22, 2017

(86) PCT No.: PCT/EP2017/084375
§ 371 (c)(1),
(2) Date: Jun. 19, 2020

(87) PCT Pub. No.: WO2019/120564
PCT Pub. Date: Jun. 27, 2019

(65) Prior Publication Data
US 2021/0113442 A1    Apr. 22, 2021

(51) Int. Cl.
| | | |
|---|---|---|
| *A61Q 19/00* | (2006.01) | |
| *A61K 8/34* | (2006.01) | |
| *A61K 8/06* | (2006.01) | |
| *A61K 8/19* | (2006.01) | |
| *A61K 8/37* | (2006.01) | |
| *A61K 8/55* | (2006.01) | |
| *A61K 8/60* | (2006.01) | |

(Continued)

(52) U.S. Cl.
CPC .............. *A61K 8/345* (2013.01); *A61K 8/062* (2013.01); *A61K 8/19* (2013.01); *A61K 8/342* (2013.01); *A61K 8/375* (2013.01); *A61K 8/55* (2013.01); *A61K 8/602* (2013.01); *A61K 8/891* (2013.01); *A61K 8/92* (2013.01); *A61Q 19/00* (2013.01); *A61K 2800/30* (2013.01)

(58) Field of Classification Search
CPC .......... A61Q 19/00; A61K 8/345; A61K 8/06; A61K 8/062; A61K 8/375; A61K 8/342; A61K 2800/52; A61K 2800/30; A61K 8/19; A61K 8/92
USPC ....................................................... 424/70.1
See application file for complete search history.

(56) References Cited

U.S. PATENT DOCUMENTS

| | | | | |
|---|---|---|---|---|
| 2007/0092478 A1* | 4/2007 | Behrens | ................ | A61K 8/345 424/70.31 |
| 2010/0324152 A1* | 12/2010 | Schmaus | ................ | A61Q 19/10 514/738 |

(Continued)

FOREIGN PATENT DOCUMENTS

| | | |
|---|---|---|
| CN | 104027270 A | 9/2014 |
| DE | 10308565 A1 | 9/2004 |

(Continued)

OTHER PUBLICATIONS

International Search Report and Written Opinion dated Aug. 24, 2018 for corresponding PCT Application No. PCT/EP2017/084375.

(Continued)

*Primary Examiner* — Eisa B Elhilo
(74) *Attorney, Agent, or Firm* — Polsinelli PC (57) ABSTRACT

The present invention relates to novel cosmetic emulsions, comprising 1,2-decanediol, advantageous uses thereof and methods for their production.

16 Claims, 5 Drawing Sheets

(51) Int. Cl.
A61K 8/891 (2006.01)
A61K 8/92 (2006.01)

(56) References Cited

U.S. PATENT DOCUMENTS

| | | | | |
|---|---|---|---|---|
| 2015/0190326 A1* | 7/2015 | Brouard | .................. | A61K 8/37 |
| | | | | 514/777 |
| 2015/0374599 A1* | 12/2015 | Schmaus | ................ | C11D 7/264 |
| | | | | 510/102 |
| 2016/0206571 A1* | 7/2016 | Schmaus | .................. | A61K 9/14 |
| 2017/0296444 A1* | 10/2017 | Skubsch | ................ | A61K 8/046 |
| 2017/0296445 A1* | 10/2017 | Skubsch | ................ | A61K 8/046 |

FOREIGN PATENT DOCUMENTS

| | | | |
|---|---|---|---|
| EP | 1872770 | A2 | 1/2008 |
| EP | 2243462 | A1 | 10/2010 |
| EP | 2589291 | A1 | 5/2013 |
| EP | 2745831 | A1 | 6/2014 |
| EP | 3045161 | A1 | 7/2016 |

OTHER PUBLICATIONS

Database GNPD [online] MINTEL; Dec. 1, 2010 (Dec. 1, 2010), BOSCIA: "Clear Complexion Moisturizer with Botanical Blast", XP002743241, Database accession No. 1448967.

* cited by examiner

COSMETIC EMULSION COMPRISING 1,2-DECANEDIOL

CROSS-REFERENCE TO RELATED APPLICATIONS

This application is a national stage application (under 35 U.S.C. § 371) of PCT/EP2017/084375, filed Dec. 22, 2017, which is incorporated herein by reference in its entirety.

The skin is an important but at the same time sensible organ, the care of which is essential for health and physical as well as mental well-being. Due to this reason, already a plenty of skin care products and cosmetics have been developed which are available as for example creams, lotions, oils, sprays or gels and contain different skin care agents.

Often, skin care products and cosmetics are present in form of emulsions. Emulsions are heterogeneous systems of at least two, usually non-mixable liquids (phases), wherein one liquid (phase) forms small droplets which are distributed in the other liquid (phase). The phase forming the droplets is designated as the disperse phase. The phase containing the droplets is designated as the continuous phase.

The most important emulsions in the cosmetic industry are oil-in-water (O/W) and water-in-oil (W/O) emulsions. These emulsions are also described as single-emulsions. O/W emulsions have water as their continuous phase and an oil as disperse phase. W/O emulsions have an oil as continuous phase and water as disperse phase. The basic characteristic of an O/W emulsion is determined by the water. The basic characteristic of a W/O emulsion is determined by the oil.

Within the scope of the present invention, the term "oil" is understood as an organic liquid, which is not mixable with water under normal circumstances. In cosmetic emulsions, usually deionized water (also known as demineralized water, distilled water or ultra-pure water) is used.

An important characteristic of a cosmetic emulsion is, in addition to its cosmetic effectiveness, its physical stability. Also, a homogenous and stable appearing emulsion can change with increasing storage time. These changes can be unseen or lead to a clearly visible phase separation, a so-called "breaking" of the emulsion with clearly visible separation of water or oil. These processes can influence the emulsion-characteristic attributes in such a way that the emulsion no longer fulfils the expectations, e.g. to a cosmetic product, and becomes useless.

Without being bound by a certain theory, the undesired phase separation underlies the thermodynamic instability of an emulsion which is the result of an, under normal circumstances, high interfacial tension between the phases, which in turn is a result of the different intramolecular attraction forces within the respective phase. Emulsions thus show a general effort to a possibly low interface between the single (under normal circumstances non-mixable) phases and thus to a separation of the phases.

To counteract this effort and to keep emulsions stable over a longer time, emulsifiers are typically added to emulsions, which reduce the surface or, respectively, interfacial tension of the emulsions. Emulsifiers are molecules with a polar, hydrophilic (water-loving) structural element and a non-polar lipophilic (oil-loving) structural element. Due to its amphiphilic characters, the single emulsifier molecules accumulate at the interfaces and reduce the surface or, respectively, interfacial tension. Together with an addition of mechanical work and, where necessary, thermic energy, a finely disperse system arises in which one phase is finely distributed and present in the form of droplets in the other phase.

There is thus the general need of compounds which reduce the surface or, respectively, interfacial tension of an emulsion. Particularly, there is the need of compounds which strongly reduce the surface or, respectively, interfacial tension of an emulsion already in low amounts.

A class of compounds which is awarded surface or, respectively, interfacial tension reducing characteristics, is 1,2-alkanediols.

1,2-alkanediols are also described as wetting agents. These reduce the interfacial tension between aqueous phase and oil phase, but alone they are not capable of forming stable emulsions. Consequently, 1,2-alkanediols are not classified as emulsifying substances (emulsifiers) according to the concept of Griffin (cf. Griffin, W. C.: Classification of surface active agents by HLB, J. Soc. Cosmet. Chem. 1, 1949).

In addition to a surface or, respectively, interfacial tension reducing characteristic, 1,2-alkanediols are also awarded further positive characteristics, such as for example moisturizing or antimicrobial characteristics.

Thus, in the state of the art, the use of 1,2-alkanediols in cosmetic emulsions as well as cosmetic emulsions which comprise 1,2-alkanediols are known.

The use of 1,2-decanediol, 1,2-octanediol, 1,2-hexanediol and 1,2-pentanediol in cosmetic or dermatologically effective amounts is known from EP 2 589 291.

DE 10 2012 224 158 describes a cosmetic emulsion comprising polyglycerol-3-methylglucose distearate, silica dimethyl silylates and acrylates/c10-c30 alkylacrylate crosspolymer.

EP 1 946 742 describes a cosmetic water-in-silicon oil emulsion comprising 1,2-decanediol.

EP 1 426 029 A1 describes an emulsion comprising 1,2-alkanediols which is stable for long time.

A further problem of cosmetic emulsions is that emulsifiers are generally required for imparting the emulsion a certain (physical) stability, but these emulsifiers do typically not show a cosmetic effect. It is thus desirable to keep the total amount of emulsifiers (i.e. the total amount of all emulsifiers in the emulsion) as low as possible, but at the same time without reducing the (physical) stability of the emulsion. There thus exists the need of means and ways to reduce the total amount of emulsifiers of an emulsion, but at the same time without reducing the (physical) stability of the emulsion. Although this may appear contradicting at the first view, it is particularly desirable to reduce the total amount of emulsifiers of an emulsion and increase the (physical) stability at the same time.

It is thus an object of the present invention to reduce the amount of emulsifiers used in cosmetic emulsions but at the same time without reducing the (physical) stability of the emulsion, at the best to even increase the (physical) stability (despite the reduced total amount of emulsifiers).

This and further objects is/are solved by a cosmetic emulsion comprising
a continuous water phase,
oil droplets distributed in the continuous water phase and 1,2-decanediol,
wherein the oil droplets distributed in the continuous water phase have an average volume-related diameter $d_{v0.5}$ of from 1.0 to 10.0 µm.

Preferably, the oil droplets distributed in the continuous water phase have an average volume-related diameter $d_{v0.5}$ of from 3.0 to 10.0 µm, further preferably of from 5.0 to 10.0

μm. Even further preferably, the oil droplets distributed in the continuous water phase have an average volume-related diameter $d_{v0.5}$ of from 5.1 to 9.9 μm.

The cosmetic emulsion according to the invention is thus an O/W emulsion with a continuous water phase and a disperse oil phase.

1,2-decanediol has the following structural formula

According to the HLB-concept of Griffin, 1,2-decanediol has a HLB-value of approximately 3.9. As a comparison, 1,2-pentanediol has a HLB-value of 6.6, 1,2-hexanediol an HLB-value of 5.8 and 1,2-octanediol an HLB-value of 4.7.

Within the scope of the present invention, the average volume-based diameter of the oil droplets was preferably determined with the principle of laser diffraction spectroscopy. Corresponding machines for the determination of the average volume-based diameter are distributed by e.g. Malvern Instruments GmbH and Malvern Instruments Ltd.. As far as subsequently not indicated otherwise, the average volume-based diameter is determined with a machine of the type Malvern "Mastersizer 3000".

$d_{v0.5}$ XY means that 50% of the oil droplets have a volume-based diameter which is smaller than XY. Thus for example, $d_{v0.5}$ 20 μm means that 50% of the oil droplets have a volume-based diameter which is smaller than 20 μm.

Accordingly, $d_{v0.1}$ XY means that 10% of the oil droplets have a volume-based diameter which is smaller than XY. Thus for example, $d_{v0.1}$ 20 μm means that 10% of the oil droplets have a volume-based diameter which is smaller than 20 μm.

$d_{v0.9}$ XY means that 90% of the oil droplets have a volume-based diameter which is smaller than XY. Thus for example, $d_{v0.9}$ 20 μm means that 90% of the oil droplets have a volume-based diameter which is smaller than 20 μm.

Preferably, deionized water is used. Depending on the emulsion to be produced, also regular tap water may be used. The skilled person may chose the water to be used according to his expertise.

It is preferred that the emulsion according to the invention does not contain further 1,2-alkanediols in addition to 1,2-decanediol.

Oil Phase

Preferably, the emulsion according to the invention is a two-phase system of a cosmetic oil in water.

A cosmetic oil is to be understood according to the invention as an oil, which is skin compatible and/or has a positive cosmetic effect.

The oil used in the cosmetic emulsion according to the invention is preferably selected from the group consisting of Guerbet-Alcohols on the basis of fatty alcohols with 6 to 18, preferably 8 to 10 carbon atoms, esters of linear C6-C22 fatty acids with linear or branched C6-C22 fatty alcohols or esters of branched C6-C13 carbonic acids with linear or branched C6-C22 fatty alcohols.

Preferably, the oil used in the cosmetic emulsion according to the invention is selected from the group consisting of myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate.

Further preferred oils are esters of linear $C_6$-$C_{22}$ fatty acids with branched alcohols, particularly 2-ethyl hexanol, esters of $C_{18}$-$C_{38}$ alkylhydroxy-carbonic acids with linear or branched C6-$C_{22}$ fatty alcohols, particularly dioctyl malate, esters of linear or branched fatty acids with polyvalent alcohols (e.g. propylene glycol, dimerdiol or trimertriol), guerbet-alcohols, triglycerides based on $C_6$-$C_{10}$ fatty acids and/or liquid mono/di/triglyceride mixtures based on $C_6$-$C_{18}$ fatty acids, esters of aromatic carbonic acids, particularly benzoic acid, with $C_6$-$C_{22}$ fatty alcohols and/or guerbet-alcohols, esters of $C_2$-$C_{12}$ dicarbonic acids with linear or branched alcohols with 1 to 22 carbon atoms and/or polyols with 2 to 10 carbon atoms and 2 to 6 hydroxyl groups, vegetable oils, branched primary alcohols, substituted cyclohexanes, linear and branched $C_6$-$C_{22}$ fatty alcohol carbonates, such as dicapryl carbonate (Cetiol® CC), guerbet-carbonates based on fatty alcohols with 6 to 18, preferably 8 to 10, carbon atoms, esters of benzoic acid with linear and/or branched $C_6$-$C_{22}$ alcohols (e.g. Finsolv® TN), linear or branched, symmetric or asymmetric dialkyl ethers with 6 to 22 carbon atoms per alkyl group, e.g. dicapryl ether (Cetiol® OE), and/or ring opening products of epoxidized fatty acid esters with polyols.

Particularly suited are caprylic/capric triglyceride (also known as neutral oil) and cetearylethyl hexanoate.

Further suited are silicon oils (cyclomethicone, siliconmethicone etc.) and/or aliphatic or panthenic carbohydrates, e.g. squalanes, squalenes or dialylcyclohexanes. However, it is preferred that the emulsion according to the invention has less than 25 wt.-%, preferably less than 20 wt.-%, further preferably less than 10 wt.-%, particularly preferably less than 5 wt.-%, even further preferably 0 wt.-% of silicon-containing oils, related to the total weight of the emulsion. A silicon-containing oil is understood in the scope of the present invention as an oil which contains the structural unit $[R^1R^2SiO]_n$ in which $R^1$ and $R^2$ are for example organic residues and n is an integer.

The selection of the components of the oil phase and the composition with regard to the mass of the oil phase are mainly responsible for the spreading ability of the cosmetic emulsion on the skin, which in turn mainly influences the skin sensation.

According to a preferred embodiment, the oil phase comprises ethylhexyl isononanoate, caprylic/capric triglyceride and Prunus Amygdalus Dulcis (Sweet Almond) oil or consists thereof. It has been found that this combination of low, medium and highly spreading substances of the emulsion provide a good distribution on the skin surface and result in a pleasant skin sensation.

Particularly preferably, the oil phase comprises caprylic/capric triglyceride and cetearylethylhexanoate or consists thereof. Particularly preferably, the weight ratio of caprylic/capric triglyceride and cetearylethylhexanoate is 2:1. Particularly preferably, the oil phase comprises caprylic/capric triglyceride and cetearylethylhexanoate in a total amount of from 1.0 to 50.0 wt.-%, preferably 3.0 to 30.0 wt.-%, further preferably 5.0 to 20.0 wt.-%, further preferably 8.0 to 15.0 wt.-%, even further preferably 10.0 to 13.0 wt.-% or consists thereof, related to the total weight of the emulsion. According to a further preferred embodiment, the oil phase comprises caprylic/capric triglyceride in an amount of from 2.0 to 15.0 wt.-%, preferably 4.0 to 12.0 wt.-%, further preferably 5.0 to 10.0 wt.-% even further preferably 7.0 to 9.0 wt.-% and/or cetearylethylhexanoate in an amount of from 1.0 to 10.0 wt.-%, preferably 2.0 to 8.0 wt.-%, further preferably 3.0 to 5.0 wt.-%, or consists thereof, each related to the total weight of the emulsion. According to a particularly preferred embodiment, the oil phase comprises caprylic/capric triglyceride in an amount of from 7.0 to 9.0 wt.-% and cetearylethylhexanoate in an amount of from 3.0 to 5.0 wt.-% or consists thereof, each related to the total weight of the emulsion.

Droplet Size

According to a further preferred embodiment, the oil droplets distributed in the water phase have an average volume-based diameter $d_{v0.1}$ of from 1.0 to 10.0 µm, preferably 2.0 to 8.0 µm, further preferably 3.0 to 5.5 µm, also preferably determined by laser diffraction spectroscopy. Particularly preferably, the oil droplets distributed in the water phase have an average volume-based diameter $d_{v0.1}$ of from 3.1 to 5.4 µm.

According to a further preferred embodiment, the oil droplets distributed in the water phase have an average volume-based diameter $d_{v0.9}$ of from 1.0 to 30.0 µm, preferably 5.0 to 25.0 µm, further preferably 10.0 to 22.0 µm, even further preferably 10.0 to 16.0 µm also preferably determined by laser diffraction spectroscopy. Particularly preferably, the oil droplets distributed in the water phase have an average volume-based diameter $d_{v0.9}$ of from 10.1 to 15.9 µm.

It has been found that the size of the oil droplets distributed in the water phase is a measure for the physical stability of the emulsion. A small size results in a low surface or, respectively, interfacial tension and thus a high (physical) stability of the emulsion.

Preferably, the emulsion according to the invention is free of silica dimethylsilylate.

According to a further preferred embodiment, the emulsion according to the invention further comprises one or more different emulsifier(s) different from 1,2-decanediol.

It was surprisingly found that 1,2-decanediol has a co-emulsifying effect and by the presence of only low amounts of 1,2-decanediol in an emulsion, the total amount of emulsifiers can be significantly reduced without reducing the emulsion stability. It was particularly surprisingly found that by the presence of only low amounts of 1,2-decanediol in an emulsion, the total amount of emulsifiers can be reduced and simultaneously, the emulsion stability can be increased.

Emulsifier

Within the scope of the present invention, emulsifiers, which have an HLB-value in the range of from 8 to 18, preferably 8 to 16, are preferred.

Preferably, the one or more emulsifier(s) different from 1,2-decanediol is/are selected from the group consisting of PEG-100 stearate, cetearyl glucoside, distearyldimonium chloride, palmitamidopropyl trimoniumchloride, glyceryl stearat citrate, glyceryloleate citrate, polyglyceryl-(3)-methylglucose distearate, cetearyl alcohol, potassium cetyl phosphate, sodium cetyl phosphate, acrylate/$C_{10}$-$C_{30}$-alkylacrylate-cross-polymer, ammoniumacryloyldimethyltaurate/beheneth-25 methacrylate-cross-polymer, polyglyceryl-4-caprate, polyglyceryl-4-caprylate/caprate, cetyl PEG/PPG-10/1 dimethicon, polyglyceryl-6 dioleate, polyglyceryl-2-stearate, PEG-30 dipolyhydroxystearate, sodium stearoyllactylate, PEG-40 hydrated castor oil, hydrated palmglycerides (INCI-nomenclature: hydrogenated Palm Glycerides) or a mixture thereof.

Particularly preferably, the one or more emulsifier(s) different from 1,2-decanediol is/are selected from the group consisting of cetearyl alcohol, glycerylstearat citrate, polyglyceryl-(3)-methylglucosedistearate, potassium cetyl phosphate, hydrated palmglycerides and a mixture thereof.

Further preferably, the one or more emulsifier(s) different from 1,2-decanediol is/are selected from the group consisting of glyceryl stearate citrate, polyglyceryl-(3)-methylglucosedistearate, potassium cetyl phosphate, hydrated palmglycerides and a mixture thereof.

Further preferably, the emulsifier different from 1,2-decanediol is a mixture of cetearyl alcohol and member of the group consisting of (i) a mixture of potassium cetyl phosphate and hydrated palmglycerides (preferably in a weight ratio of from 1:1 to 7:3, particularly approximately 6:4 (potassium cetyl phosphate to hydrated palmglycerides)), (ii) glyceryl stearate citrate and (iii) polyglyceryl-(3)-methylglucosedistearate.

Further preferably, the emulsifier different from 1,2-decanediol is a mixture of cetearyl alcohol and a mixture of potassium cetyl phosphate and hydrated palmglycerides. Preferably, the weight ratio of potassium cetyl phosphate and hydrated palmglycerides in the mixture of potassium cetyl phosphate and hydrated palmglycerides is 1:1 to 7:3, particularly approximately 6:4.

According to a further preferred embodiment, the emulsifier different from 1,2-decanediol is a mixture of cetearyl alcohol and glyceryl stearate citrate. According to a further preferred embodiment, the emulsifier different from 1,2-decanediol is a mixture of cetearyl alcohol and polyglyceryl-(3)-methylglucosedistearate.

Further preferably, the emulsifier different from 1,2-decanediol is a mixture of potassium cetyl phosphate and hydrated palmglycerides, wherein the weight ratio of potassium cetyl phosphate and hydrated palmglycerides in the mixture of potassium cetyl phosphate and hydrated palmglyceridesis particularly preferably 1:1 to 7:3, particularly approximately 6:4.

Further preferably, the emulsifier different from 1,2-decanediol is glyceryl stearate citrate.

Further preferably, the emulsifier different from 1,2-decanediol is polyglyceryl-(3)-methyl-glucosedistearate.

Preferably, the one or more emulsifier(s) different from 1,2-decanediol is/are present in the emulsion in a total amount of from 0.1 to 5.0 wt.-%, preferably 0.1 to 3.0 wt.-%, further preferably 0.5 to 2.5 wt.-%, even further preferably 1.0 to 2.3 wt.-%, even further preferably 1.0 to 1.8 and most preferably 1.6 to 1.8 wt.-%, related to the total weight of the emulsion.

According to a preferred embodiment, the emulsion according to the invention comprises cetearyl alcohol in an amount of from 0.1 to 1.5 wt.-%, preferably 0.3 to 1.3 wt.-%, further preferably 0.5 to 0.9 wt.-%, particularly preferably approximately 0.7 wt.-%, related to the total weight of the emulsion and further a member of the group consisting of (i) a mixture of potassium cetyl phosphate and hydrated palmglycerides (preferably in a weight ratio of from 1:1 to 7:3, particularly approximately 6:4 (potassium cetyl phosphate to hydrated palmglycerides)), (ii) glyceryl stearate citrate and (iii) polyglyceryl-(3)-methylglucosedistearate in an amount of from 0.1 to 5.0 wt.-%, preferably 0.1 to 3.0 wt.-%, further preferably 0.5 to 2.0 wt.-%, even further preferably 0.5 to 1.5 wt.-% and most preferably 0.8 to 1.2 wt.-%, particularly approximately 1.0 wt.-%, related to the total weight of the emulsion.

Particularly preferably, the emulsion according to the invention comprises cetearyl alcohol in an amount of from 0.5 to 0.9 wt.-% and further a member of the group consisting of (i) a mixture of potassium cetyl phosphate and hydrated palmglycerides (preferably in a weight ratio of from 1:1 to 7:3, particularly approximately 6:4 (potassium cetyl phosphate to hydrated palmglycerides)), (ii) glyceryl stearate citrate and (iii) polyglyceryl-(3)-methylglucosedistearate in an amount of from 0.8 to 1.2 wt.-%, each related to the total weight of the emulsion.

1,2-Decanediol

The emulsion according to the invention comprises 1,2-decanediol. Preferably, the emulsion according to the invention comprises 1,2-decanediol in an amount of up to 2.0 wt.-%, preferably up to 1.5 wt.-%, further preferably up to 1.0 wt.-%, further preferably up to 0.5 wt.-%, further preferably up to 0.1 wt.-%, further preferably up to 0.05 wt.-%, related to the total weight of the emulsion.

According to a further preferred embodiment, the emulsion according to the invention comprises 1,2-decanediol in an amount in the range of from 0.005 to 0.1 wt.-%. Preferably, the emulsion according to the invention comprises 1,2-decanediol in an amount in the range of from 0.005 to 0.05 wt.-% or from 0.05 to 0.1 wt.-% related to the total weight of the emulsion.

Preferably, the emulsion according to the invention comprises 1,2-decanediol in an amount in the range of from 0.03 to 0.12 wt.-%, most preferably 0.08 to 0.12 wt.-% or 0.03 to 0.07 wt.-%, each related to the total weight of the emulsion. It is particularly preferred that the emulsion according to the invention comprises 1,2-decanediol in an amount of from 0.03 to 0.07 wt.-%.

It has been found that the total amount of emulsifier in an emulsion which contains 1,2-decanediol in such an amount can be significantly reduced without reducing the (physical) stability of the emulsion. Particularly, it has been found that by the presence of 1,2-decanediol in such an amount, the total amount of emulsifier can be significantly reduced and simultaneously, the (physical) stability can be even increased (despite the reduced total amount of emulsifier). This is completely unexpected as a reduced total amount of emulsifier regularly leads to a reduced stability of an emulsion.

According to a further preferred embodiment, the emulsion according to the invention comprises 1,2-decanediol in an amount of from 0.005 to 0.05 wt.-%, further preferably 0.007 to 0.012 wt.-%, even further preferably approximately 0.01 wt.-%, related to the total weight of the emulsion. It has been surprisingly found that 1,2-decanediol leads to a very strong reduction of the surface or, respectively, interfacial tension already in this very low amount, while other typically used 1,2-alkanediols such as 1,2-pentanediol, 1,2-hexanediol and 1,2-octanediol lead to no or only a negligible reduction of the surface or, respectively, interfacial tension.

It is preferred that the emulsion according to the invention has a pH value of from 4.0 to 8.0, preferably 5.0 to 6.5.

Further Components

The emulsion according to the invention can further contain additional, useful components, such as for example:

Preservatives, anti-microbial agents such as e.g. further anti-bacterial agents or fungicides, abrasives, anti-acne-agents, agents against skin aging, anti-cellulitis-agents, anti-dandruff-agents, anti-inflammatory agents, anti-irritant agents, irritation-reducing agents, anti-oxidants, astringents, anti-sweat agents, anti-septic agents, anti-statics, binders, buffers, carrier materials, chelating agents, cell stimulants, cleaning agents, caring agents, depilatories, surface-active substances, deodorants, antiperspirants, softeners, emulsifiers, enzymes, essential oils, fibres, film formers, fixators, foam formers, foam stabilizers, substances for inhibiting the foaming, foam boosters, gelling agents, hair care agents, hair forming agents, hair smoothing agents, moisturizing agents, moistening substances, humectant substances, bleaching agents, strengthening agents, stain removing agents, optically bleaching agents, impregnating agents, dirt-repellents, friction-reducing agents, lubricants, moisturizing cream, ointments, opacifiers, plastifying agents, opacifying agents, polish, brighteners, polymers, powder, proteins, re-fattening agents, grinding agents, silicones, skin calming agents, skin cleaning agents, skin caring agents, skin healing agents, skin bleaching agents, skin protecting agents, skin softening agents, cooling agents, skin cooling agents, warming agents, skin warming agents, stabilizers, UV-adsorbants, UV-filter, washing agents, fabric softeners, suspending agents, tanning agents, thickeners, rheological additives, vitamins, oils, waxes, fats, phospholipids, saturated fatty acids, singly or multiply unsaturated fatty acids, a-hydroxy acids, polyhydroxy fatty acids, liquefiers, dyes, dye-protecting agents, pigments, anti-corrosives, aromas, flavourings, aromatic substances, polyols, surfactants, electrolytes, organic solvents or silicon derivatives.

The cosmetic emulsion according to the invention can also contain sweat inhibiting active substances (anti-transpirants) and be used for example as deodorant for reducing body odour. Sweat inhibiting active substances are especial aluminium salts such as aluminium chloride, aluminium chlorhydrate, -nitrate, -sulfate, -acetate etc. Also the use of zinc, magnesium and zirconium compounds can be advantageous. Particularly, the aluminium salts and—in slightly lower extent—aluminium/zirconium salt combinations have proven well. Also worth mentioning are the partially neutralized and thus more skin compatible but not such effective aluminium hydroxyl chlorides.

Preferably, the emulsion according to the invention also acts as sun blocking agents. Thus, the emulsion according to the invention preferably contains at least one UVA-filter and/or at least one UVB-filter and/or at least one wide-range-filter and/or at least on inorganic pigment.

Preferably, the emulsion according to the invention contains at least one UVA-filter and/or at least one UVB-filter and/or at least one wide-range-filter and/or at least on inorganic pigment in a total amount of from 0.01 wt.-% to 40 wt.-%, preferably 0.1 wt.-% to 10 wt.-%, particularly 1.0 to 5.0 wt.-%, related to the total weight of the emulsion.

Vitamins

Preferably, the emulsion according to the invention contains vitamins and/or vitamin precursors, wherein all vitamins and vitamin precursors suitable for cosmetic and/or dermatologic applications or all typical vitamins and vitamin precursors can be used. Worth mentioning are particularly vitamins and vitamin precursors such as tocopherols, vitamin A, nicotinic acid and nicotinic acid amides, further vitamins of the B-complex, particularly biotin and vitamin C, panthenol and its derivatives, particularly the esters and ethers of panthenol, as well as cationic derivatized panthenols such as e.g. panthenol triacetate, panthenol monoethyl ether and its monoacetate as well as cationic panthenol derivatives.

Rheological Additives

Particularly preferably, the cosmetic emulsion according to the invention further contains one or more rheological additive(s). Rheological additives are understood as additives, which exert a rheological effect, such as increasing the viscosity, in the cosmetic emulsion.

Suitable rheological additives are for example polymeric compounds such as for example such of the Aerosil®-type (hydrophilic silicon dioxide), polysaccharides, preferably xanthangum, guar-gum, agar-agar, alginates and tyloses, carboxymethyl cellulose and hydroxyethyl cellulose, polyethylene glycol monoester and diesters of fatty acid with rather high molecular weight, polyacrylates (e.g. carbomer, Carbopole® [Goodrich] or Synthalene® [Sigma]), polyacrylamides, polyvinyl alcohols and polyvinyl pyrrolidon, surfactants such as for example ethoxylated fatty acid glycerides, esters of fatty acids with polyols, for example pentaerythritol or trimethylol propane, narrow band fatty alcoholethoxylates and electrolytes such as for example sodium chloride and ammonium chloride or a mixture thereof.

Preferably, carbomer and/or xanthan-gum are used as rheological additives. These are hydrophilic gel formers and form a connected three-dimensional network which binds liquid. Carbomer and xanthan-gum thicken the continuous phase of the emulsion according to the invention which further increases the (physical) stability of the emulsion.

If carbomer (which is an acrylic acid polymerizate) is used as rheological additive, the emulsion according to the invention preferably has a pH-value in the range of from 5 to 11, further preferably 5 to 10, particularly preferably 5.5 to 6.5. Because the viscosity resulting from the carbomer is also dependent from the adjusted pH-value as is the amount of use, wherein the maximum viscosity is achieved at a pH-value of 6 to 10. If carbomer is used as rheological additive, the emulsion according to the invention is preferably free of cationic substances and/or electrolytes and/or polyvalent metal ions.

For adjusting the pH-value, preferably an aqueous sodium hydroxide solution, preferably 10% (mass percentage) is used.

The rheological additive(s) is/are preferably each present in an amount of from 0.01 to 3.0 wt.-%, preferably 0.01 to 2.0 wt.-%, more preferably 0.01 to 1.0 wt.-%, further preferably 0.01 to 0.5 wt.-%, further preferably 0.05 to 0.15 wt.-%, even further preferably approximately 0.1 wt.-% in the emulsion according to the invention, related to the total weight of the emulsion.

Particularly preferably, the emulsion according to the invention contains carbomer and/or xanthan-gum in an amount of each 0.1 wt.-%, related to the total weight of the emulsion.

The emulsion according to the invention is preferably a skin care agent, hair care agent or a sun blocker. Preferably the emulsion according to the invention is present in form of a cream, a lotion, a spray, an ointment or a gel. Particularly preferably, the emulsion according to the invention is a skin lotion, a hair shampoo, a shower gel, an anti-transpirant, a deodorant or a soap.

Use

The present invention further relates to the use of 1,2-decanediol for reducing the surface or, respectively, interfacial tension of a cosmetic emulsion. Preferably, 1,2-decanediol is used in an emulsion according to the invention as described above for reducing the surface or, respectively, interfacial tension.

It was surprisingly found that 1,2-decanediol reduces the surface or, respectively, interfacial tension in an exceptionally strong manner. This allows a use of 1,2-decanediol in very low amounts, particularly in amounts in which other 1,2-alkanediols as for example 1,2-penatediol, 1,2-hexanediol and 1,2-octanediol do not or only in a little extent reduce the surface or, respectively, interfacial tension.

The present invention further relates to the use of 1,2-decanediol as co-emulsifier for reducing the total amount of emulsifier in a cosmetic emulsion. Preferably, 1,2-decanediol is used as co-emulsifier for reducing the total amount of emulsifier in an emulsion according to the invention as described above.

It was surprisingly found that the total amount of emulsifier of an emulsion which contains low amounts of 1,2-decanediol, can be significantly reduced without reducing the (physical) stability.

Method

The present invention further relates to a method for producing the emulsion according to the invention. The method comprises the following steps or consists thereof: a) providing an aqueous phase; b) providing an oil phase; c) combining the aqueous phase and the oil phase, wherein the aqueous phase and/or the oil phase comprises 1,2-decanediol.

According to an embodiment, the aqueous phase comprises 1,2-decanediol. According to another embodiment, the oil phase comprises 1,2-decanediol. According to a further embodiment, the aqueous phase and the oil phase comprise 1,2-decanediol.

Preferably, the aqueous phase and/or the oil phase is/are heated before step c), which leads to a good homogenisation of the phases.

In connection therewith, it was found that a particularly good homogenisation is achieved if the phases are heated to a temperature of from 50 to 100° C., particularly if the aqueous phase is heated to a temperature in a range of from 70 to 90° C., preferably approximately 80° C., and if the oil phase is heated to a temperature in a range of from 80 to 100° C., preferably approximately 90° C.

Thus, the phases are preferably heated to a temperature of from 50 to 100° C. Particularly preferably, the aqueous phase is heated to a temperature in a range of from 70 to 90° C., preferably approximately 80° C., and the oil phase is heated to a temperature in a range of from 80 to 100° C., preferably approximately 90° C. This led to the best results.

If the emulsion according to the invention comprises one or more rheological additive(s), preferably, the oil phase is provided first, by combining and mixing the single components but without the rheological additive(s). Subsequently, this mixture is heated, preferably to the temperature indicated above and then subsequently, the rheological additive(s) is/are added.

Preferably, the phases combined in step c) are homogenized. Therefore, preferably a sprocket dispersion unit (IKA® T25 digital ULTRA TURRAX®) is used. Particularly preferably, the homogenization is applied for three minutes at 6000 U/min.

Subsequently (after accomplished homogenization), the obtained emulsion can be adjusted to the desired pH-value with a sodium hydroxide solution, preferably 10% (mass percentage) and by stirring, preferably with a stirring paddle, particularly preferably at 150 U/min. If carbomer is used as rheological additive, the obtained emulsion is preferably adjusted to a pH-value in the range of from 5-11, preferably 5-10, particularly preferably 5.5 to 6.5.

This pH-value has the additional advantage that the protective acid mantle of the skin is not attached, which leads to a good skin compatibility.

After adjusting the desired pH-value, the emulsion is cooled, preferably carefully, by further stirring for 10 minutes at 150 U/min, 10 minutes at 100 U/min and 5 minutes at 50 U/min, until the emulsion has a temperature of approximately 43° C. at the end of the stirring process.

EXAMPLES

Subsequently, preferred embodiments of the present invention are further described by means of examples.

Example 1

Influence of Different 1,2-alkanediols on the Surface Tension 1,2-pentanediol, 1,2-hexanediol, 1,2-octanediol and 1,2-decanediol were used as 1,2-alkanediols. Deionized water was used as medium.

The surface tension of aqueous solutions of the different 1,2-alkanediols was determined with a drop volume tensiometer (LAUDA TVT2) according to the principle of the drop-volume-method. The precision syringe, the capillary and the water were tempered to a temperature of 20±1° C.

The volume flow was 0.5 seconds per microliter [s/μl]. The radius of the used capillary was 0.39 mm.

The 1,2-alkanediols were used in the following amounts (wt.-%, related to the total weight of the mixture):

TABLE 1

| Solution | 1,2-Alkandiol | Amount [wt.-%] |
|---|---|---|
| 1 | 1,2-Pentanediol | 0.01; 0.5 |
| 2 | 1,2-Hexanediol | 0.01; 0.5 |
| 3 | 1,2-Octanediol | 0.01; 0.5 |
| 4 | 1,2-Decanediol | 0.01 |

The low solubility of 1,2-decanediol in water did not allow a measurement at an amount of 0.5 wt.-%. The measurements of the solutions 1 to 3 at an amount of 0.5 wt.-% served for verifying that these 1,2-alkanediols (1,2-pentanediol, 1,2-hexanediol and 1,2-octanediol) can reduce the surface tension in general, however, higher amounts than 0.01 wt.-% are needed (see below).

The measurement of the surface tension is applied in triple determination, wherein each single measurement is the mean of the measurements of five falling drops. The values shown in table 2 are calculated by calculating the mean of the triple determination.

The results are shown in table 2:

TABLE 2

| | Surface tension [mN/m] | | |
|---|---|---|---|
| | 0 wt.-%* | 0.01 wt.-% | 0.5 wt.-% |
| 1,2-Pentanediol | 69.23 | 69.51 | 64.80 |
| 1,2-Hexanediol | 69.23 | 69.31 | 55.93 |

TABLE 2-continued

| | Surface tension [mN/m] | | |
|---|---|---|---|
| | 0 wt.-%* | 0.01 wt.-% | 0.5 wt.-% |
| 1,2-Octanediol | 69.23 | 66.64 | 27.97 |
| 1,2-Decanediol | 69.23 | 38.25 | — |

*comparative example

It has been found that 1,2-decanediol reduced the surface tension of water (which determines the basic characteristics of an O/W emulsion) in an exceptionally strong manner already at an amount of only 0.01 wt.-%, whereas 1,2-pentanediol and 1,2-hexanediol did not result in a reduction of the surface tension and 1,2-octanediol resulted in a negligible reduction of the surface tension.

The fact that 1,2-pentanediol and 1,2-hexanediol show a slight increase of the surface tension already at an amount of 0.01 wt.-% is probably a result of measurement inaccuracy. It was verified by measurements with an amount of 0.5 wt.-% that these 1,2-alkanediols also and indeed reduce the surface tension. It is surprisingly visible that 1,2-pentanediol and 1,2-hexanediol at an amount of 0.5 wt.-% do not reduce the surface tension even roughly as good as 1,2-decanediol at an amount of only 0.01 wt.-%. Even 1,2-octanediol, which only differs from 1,2-decanediol by two additional CH2 groups, reduces the surface tension at an amount of 0.5 wt.-% only negligibly stronger as 1,2-decanediol at an amount of only 0.01 wt.-%

Example 2

Co-Emulsifying Effect of 1,2-decanedoil and Reduction of the Total Amount of Emulsifier.

The co-emulsifying effect of 1,2-decanediol and the possibility to significantly reduce the total amount of emulsifier of an emulsion by the addition of only small amounts of 1,2-decanediol without reducing the (physical) stability was examined by three market relevant emulsifiers/emulsifier systems, which are
 (i) cetearyl alcohol and a mixture of potassium cetyl phosphate and hydrated palmglycerides (the weight ratio of potassium cetyl phosphate to hydrated palmglycerides in the mixture of potassium cetyl phosphate and hydrated palmglycerides was 6:4),
 (ii) cetearyl alcohol and glyceryl stearate citrate and
 (iii) cetearyl alcohol and polyglyceryl-(3)-methylglucose-distearate.

The model emulsions shown in tables 3 to 5 were produced. The sources of the respective components are listed in the following tables.

TABLE 3

| | | Emulsion | | | |
|---|---|---|---|---|---|
| Phase | Component | 1* | 2 | 3 | 4 |
| A | Potassium cetyl phosphate, hydrated palm glycerides (INCI-Nomenclature: Potassium Cetyl Phosphate, Hydrogenated Palm Glycerides) | 2.0 wt.-% | 2.0 wt.-% | 1.0 wt.-% | 1.0 wt.-% |
| | 1,2-Decanediol, ex Symrise AG | — | 0.1 wt.-% | 0.1 wt.-% | 0.05 wt.-% |
| | Cetearyl alcohol, ex BASF | 0.7 wt.-% | 0.7 wt.-% | 0.7 wt.-% | 0.7 wt.-% |

TABLE 3-continued

| Phase | Component | Emulsion 1* | 2 | 3 | 4 |
|---|---|---|---|---|---|
| | Caprylic/Capric Triglyceride, ex IOI | 8.0 wt.-% | 8.0 wt.-% | 8.0 wt.-% | 8.0 wt.-% |
| | Cetearylethyl hexanoate, ex Symrise AG | 4.0 wt.-% | 4.0 wt.-% | 4.0 wt.-% | 4.0 wt.-% |
| | Dimethicon, ex Evonik | 0.1 wt.-% | 0.1 wt.-% | 0.1 wt.-% | 0.1 wt.-% |
| B | Water (deionised) | 83.4 wt.-% | 83.3 wt.-% | 84.3 wt.-% | 84.35 wt.-% |
| | Glycerine, ex IOI | 1.8 wt.-% | 1.8 wt.-% | 1.8 wt.-% | 1.8 wt.-% |
| | pH-value | 5.9 | 5.8 | 5.9 | 5.9 |

*comparative example

TABLE 4

| Phase | Component | Emulsion 5* | 6 | 7 | 8 |
|---|---|---|---|---|---|
| A | Glyceryl stearate citrate, ex Symrise AG | 2.0 wt.-% | 2.0 wt.-% | 1.0 wt.-% | 1.0 wt.-% |
| | 1,2-Decanediol, ex Symrise AG | — | 0.1 wt.-% | 0.1 wt.-% | 0.05 wt.-% |
| | Cetearyl alcohol, ex BASF | 0.7 wt.-% | 0.7 wt.-% | 0.7 wt.-% | 0.7 wt.-% |
| | Caprylic/Capric Triglyceride, ex IOI | 8.0 wt.-% | 8.0 wt.-% | 8.0 wt.-% | 8.0 wt.-% |
| | Cetearylethyl hexanoate, ex Symrise AG | 4.0 wt.-% | 4.0 wt.-% | 4.0 wt.-% | 4.0 wt.-% |
| | Dimethicon, ex Evonik | 0.1 wt.-% | 0.1 wt.-% | 0.1 wt.-% | 0.1 wt.-% |
| B | Water (deionised) | 83.4 wt.-% | 83.3 wt.-% | 84.3 wt.-% | 84.35 wt.-% |
| | Glycerine, ex IOI | 1.8 wt.-% | 1.8 wt.-% | 1.8 wt.-% | 1.8 wt.-% |
| | pH-value | 6.2 | 6.1 | 6.2 | 6.1 |

*comparative example

TABLE 5

| Phase | Component | Emulsion 9* | 10 | 11 |
|---|---|---|---|---|
| A | Polyglyceryl-(3)-Methylglucose distearate, ex Evonik | 2.0 wt.-% | 2.0 wt.-% | 1.0 wt.-% |
| | 1,2-Decanediol, ex Symrise AG | — | 0.1 wt.-% | 0.1 wt.-% |
| | Cetearyl alcohol, ex BASF | 0.7 wt.-% | 0.7 wt.-% | 0.7 wt.-% |
| | Caprylic/Capric Triglyceride, ex IOI | 8.0 wt.-% | 8.0 wt.-% | 8.0 wt.-% |
| | Cetearylethyl hexanoate, ex Symrise AG | 4.0 wt.-% | 4.0 wt.-% | 4.0 wt.-% |
| | Dimethicon, ex Evonik | 0.1 wt.-% | 0.1 wt.-% | 0.1 wt.-% |
| B | Water (deionised) | 83.4 wt.-% | 83.3 wt.-% | 84.3 wt.-% |
| | Glycerine, ex IOI | 1.8 wt.-% | 1.8 wt.-% | 1.8 wt.-% |
| | pH-value | 7.1 | 7.0 | 6.9 |

*comparative example

The model emulsions were produced as follows: The components of phases A (oil phase) and B (water phase) were mixed and phases A and B were each heated to 80° C. Subsequently, phase B was added to phase A and emulsified with an IKA T25 digital Ultra TURRAX mixer for 3 minutes at 6000 U/min. The emulsions were cooled to room temperature while stirring with a paddle stirrer.

As the size of the oil droplets distributed in the continuous water phase are a measure for the (physical) stability of the emulsion, the oil droplet size (volume-based diameter) of the different model emulsions was determined.

The oil droplet size (volume-based diameter) was determined with a machine of the type Malvern "Mastersizer 3000". Solvent: Water/ethanol (90:10 (volume ratio)), saturation: maximum 10%, pump speed: 1940 U/min, duration of dispersion: 2 minutes.

Figure 1:
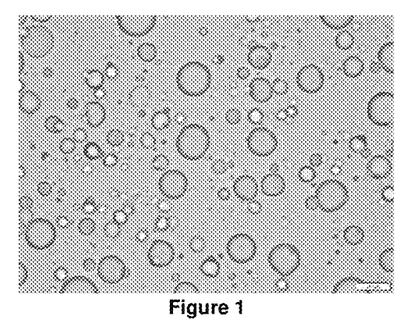
FIG. 1 shows a light microscope picture of emulsion 1.
Figure 2:
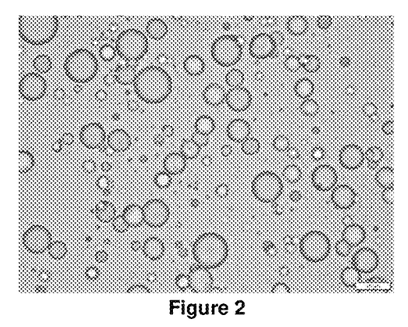
FIG. 2 shows a light microscope picture of emulsion 2.
Figure 3:
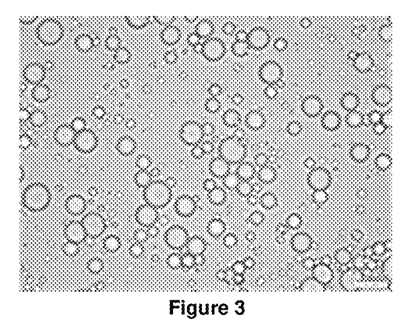
FIG. 3 shows a light microscope picture of emulsion 3.
Figure 4:
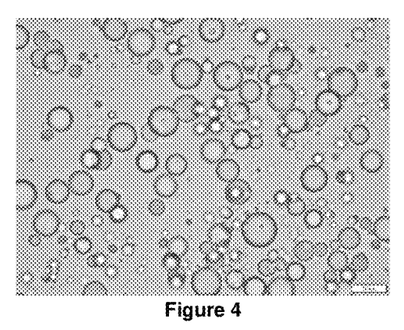
FIG. 4 shows a light microscope picture of emulsion 4.
Figure 5:
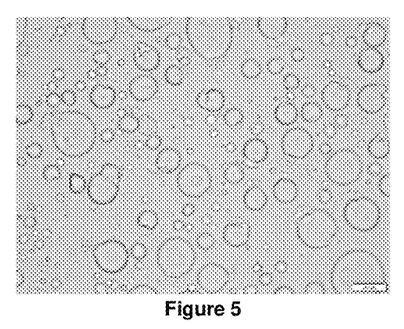
FIG. 5 shows a light microscope picture of emulsion 5.
Figure 6:
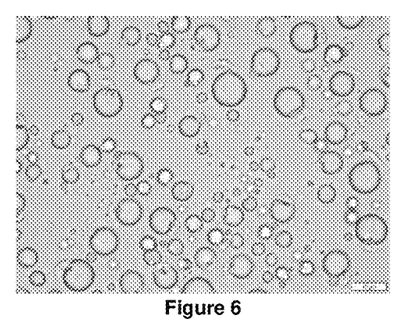
FIG. 6 shows a light microscope picture of emulsion 6.
Figure 7:
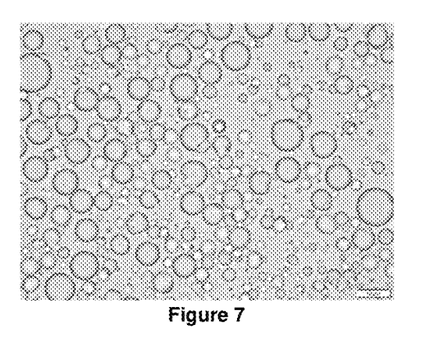
FIG. 7 shows a light microscope picture of emulsion 7.
Figure 8:
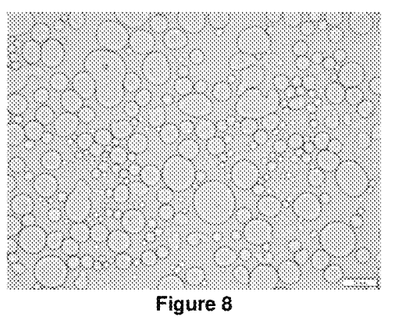
FIG. 8 shows a light microscope picture of emulsion 8.
Figure 9:
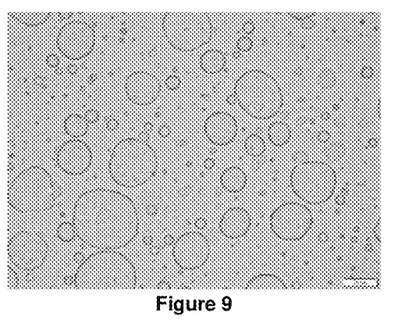
FIG. 9 shows a light microscope picture of emulsion 9.
Figure 10:
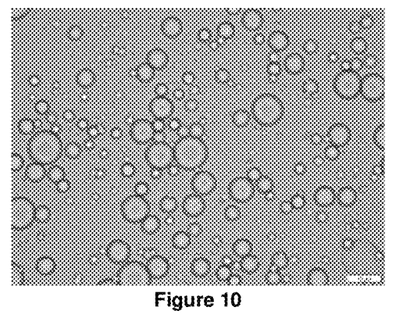
FIG. 10 shows a light microscope picture of emulsion 10.
Figure 11:
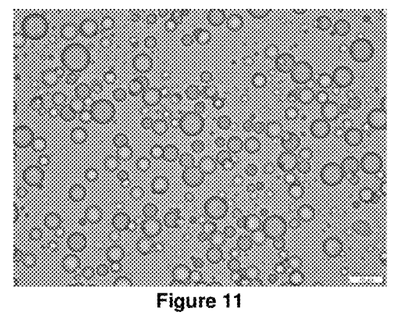
FIG. 11 shows a light microscope picture of emulsion 11.

The results are shown in Table 6 as well as in FIGS. 1 to 11. FIGS. 1 to 11 show pictures of light microscopy of the emulsions 1 to 11 (taken with a light microscope of the type Olympus IX-70, 60-times magnification).

TABLE 6

| Emulsion | $d_{v0,1}$ [μm] | $d_{v0,5}$ [μm] | $d_{v0,9}$ [μm] |
|---|---|---|---|
| 1* | 5.14 | 9.15 | 15.95 |
| 2 | 3.79 | 7.30 | 13.25 |
| 3 | 4.18 | 7.22 | 12.10 |
| 4 | 4.33 | 7.61 | 13.90 |
| 5* | 5.67 | 10.05 | 16.65 |
| 6 | 5.35 | 9.59 | 15.90 |
| 7 | 4.21 | 7.58 | 12.85 |
| 8 | 4.56 | 8.02 | 13.60 |
| 9* | 4.74 | 9.59 | 18.10 |

TABLE 6-continued

| Emulsion | $d_{v0,1}$ [μm] | $d_{v0,5}$ [μm] | $d_{v0,9}$ [μm] |
|---|---|---|---|
| 10 | 3.86 | 8.35 | — |
| 11 | 3.21 | 5.86 | 10.45 |

*comparative example

As shown in Table 6, the emulsions according to the invention (i.e. containing 1,2-decanediol) have a smaller oil droplet size and thus a higher (physical) stability than the comparative emulsions (emulsions 1, 5, 9).

Particularly, Table 6 and FIGS. 1 to 11 show that the presence of only 0.1 wt.-% or, respectively 0.05 wt.-% 1,2-decanediol allow to significantly (more than 30%) reduce the total amount of emulsifier without reducing the (physical) stability of the emulsion. This is particularly shown by a comparison of emulsions 3, 4 and 1*, of emulsions 7,8 and 5* as well as emulsions 11 and 9*. It was particularly surprisingly found that the emulsions containing 1,2-decanediol even showed a higher stability (i.e. lower oil droplet size) than the comparative emulsions despite the reduced total amount of emulsifier.

The invention claimed is:

1. A cosmetic oil-in-water emulsion comprising:
   (a) a continuous water phase;
   (b) oil droplets distributed in the continuous water phase having an average volume-related diameter $d_{v0.5}$ of 1.0 to 10.0 μm, determined by laser diffraction spectroscopy;
   (c) 0.005 to 0.1 wt.-% of 1,2-decanediol; and
   (d) 0.1 to 5.0 wt.-% of an emulsifier other than the 1,2-decanediol;
   wherein all percentages by weight are based on a total weight of the emulsion.

2. The emulsion according to claim 1, wherein the emulsion is free of silica dimethylsilylate.

3. The emulsion according to claim 1, wherein the one or more emulsifier(s) different from the 1,2-decanediol is/are selected from PEG-100 stearate, cetearyl glucoside, distearyldimonium chloride, palmitamidopropyl trimoniumchloride, glyceryl stearat citrate, glyceryloleate citrate, polyglyceryl-(3)-methylglucose distearate, cetearyl alcohol, potassium cetyl phosphate, sodium cetyl phosphate, acrylate/$C_{10}$-$C_{30}$-alkylacrylate-cross-polymer, ammoniumacryloyldimethyltaurate/beheneth-25 methacrylate-cross-polymer, polyglyceryl-4-caprate, polyglyceryl-4-caprylate/caprate, cetyl PEG/PPG-10/1 dimethicon, polyglyceryl-6 dioleate, polyglyceryl-2-stearate, PEG-30 dipolyhydroxystearate, sodium stearoyllactylate, PEG-40 hydrated castor oil, hydrated palmglycerides, and a mixture thereof.

4. The emulsion according to claim 3, wherein the one or more emulsifier(s) different from the 1,2-decanediol is/are selected from cetearyl alcohol, glycerylstearat citrate, polyglyceryl-(3)-methylglucosedistearate, potassium cetyl phosphate, hydrated palmglycerides, and a mixture thereof.

5. The emulsion according to claim 1, wherein the emulsion is a two-phase system.

6. The emulsion according to claim 1, wherein the emulsion has less than 25 wt.-% of silicon-containing oils, relative to the total weight of the emulsion.

7. The emulsion according to claim 1, wherein the oil droplets distributed in the continuous water phase have an average volume-based diameter $d_{v0.1}$ of from 1.0 to 10.0 μm, determined by laser diffraction spectroscopy.

8. The emulsion according to claim 1, wherein the oil droplets distributed in the water phase have an average volume-based diameter $d_{v\,0.9}$ of 1.0 to 30.0 μm, determined by laser diffraction spectroscopy.

9. A method for producing a cosmetic emulsion according to claim 1, comprising:
   a) providing an aqueous phase;
   b) providing an oil phase;
   c) combining the aqueous phase and the oil phase, wherein the aqueous phase and/or the oil phase comprises 1,2-decanediol.

10. The method according to claim 9, wherein the aqueous phase and/or the oil phase is/are heated before c) to a temperature of 50 to 100° C.

11. The method according to claim 9, wherein the combined phases are homogenized after c).

12. The emulsion according to claim 1, wherein the oil droplets distributed in the continuous water phase have an average volume-related diameter $d_{v0.5}$ of 3.0 to 10.0 μm, determined by laser diffraction spectroscopy.

13. The emulsion according to claim 1, wherein the oil droplets distributed in the continuous water phase have an average volume-related diameter $d_{v0.5}$ of 5.0 to 10.0 μm, determined by laser diffraction spectroscopy.

14. The emulsion according to claim 1, wherein the oil droplets distributed in the water phase have an average volume-based diameter $d_{v0.1}$ of 2.0 to 8.0 μm, determined by laser diffraction spectroscopy.

15. The emulsion according to claim 1, wherein the oil droplets distributed in the water phase have an average volume-based diameter $d_{v0.9}$ of 10.0 to 22.0 μm, determined by laser diffraction spectroscopy.

16. The emulsion according to claim 1, wherein the oil droplets distributed in the water phase have an average volume-based diameter $d_{v0.1}$ of 3.0 to 5.5 μm, an average volume-related diameter $d_{v0.5}$ of 5.0 to 10.0 μm, and an average volume-based diameter $d_{v0.9}$ of 10.0 to 16.0 μm, determined by laser diffraction spectroscopy.

* * * * *